(12) United States Patent
Cosgrove et al.

(10) Patent No.: US 8,883,802 B2
(45) Date of Patent: Nov. 11, 2014

(54) CO-CRYSTALS OF A TRIAZOLO [4,5-D] PYRIMIDE PLATELET AGGREGATION INHIBITOR

(75) Inventors: Stephen David Cosgrove, Macclesfield (GB); Matthew Jonathan Jones, Södertälje (SE); Anna Polyakova-Akkus, West Lafayette, IN (US); Valeriya Nikolayevna Smolenskaya, West Lafayette, IN (US); Brenton Skylar Wolfe, West Lafayette, IN (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 13/513,482

(22) PCT Filed: Dec. 3, 2010

(86) PCT No.: PCT/GB2010/002222
§ 371 (c)(1),
(2), (4) Date: Oct. 18, 2012

(87) PCT Pub. No.: WO2011/067571
PCT Pub. Date: Jun. 9, 2011

(65) Prior Publication Data
US 2013/0040970 A1    Feb. 14, 2013

Related U.S. Application Data

(60) Provisional application No. 61/266,307, filed on Dec. 3, 2009.

(51) Int. Cl.
*A61K 31/519* (2006.01)
*C07D 471/00* (2006.01)

(52) U.S. Cl.
USPC ........................................ 514/261.1; 544/254

(58) Field of Classification Search
USPC ........................................ 544/254; 514/261.1
See application file for complete search history.

(56) References Cited

FOREIGN PATENT DOCUMENTS

| WO | 0192262 | 12/2001 |
|---|---|---|
| WO | WO 01/92262 | * 12/2001 |

OTHER PUBLICATIONS

Stahly "Diversity in single-and multiple-component crystals. The search for and prevalence of polymorphs and cocrystals," Crystal Growth & Design (2007) 7(6):1007-1026.

Shan et al., "The role of cocrystals in pharmaceutical science," Drug Discovery Today (2008) 13(9-10):440-446.

Nehm et al., "Phase solubility diagrams of cocrystals are explained by solubility product and solution complexation," Crystal Grown & Design (2006) 6:592-600.

* cited by examiner

*Primary Examiner* — Rei-tsang Shiao
(74) *Attorney, Agent, or Firm* — Pepper Hamilton LLP

(57) ABSTRACT

The present invention relates to novel co-crystal forms of the compound of formula (I); wherein the co-former molecule is selected from glycolic acid, salicylic acid, decanoic (capric) acid, gentisic acid (2,5-dihydroxybenzoic acid), glutaric acid, vanillic acid (4-hydroxy-3-methoxybenzoic acid), succinic acid, malonic acid or maltol (3-hydroxy-2-methyl-4-pyrone); and to processes for their preparation, to pharmaceutical compositions containing such co-crystals, to the use of such co-crystals in the manufacture of a medicament for use in the prevention of arterial thrombotic complications in patients with coronary artery, cerebrovascular or peripheral vascular disease and to methods of treating such diseases in the human or animal body by administering a therapeutically effective amount of a co-crystal of the compound of formula (I).

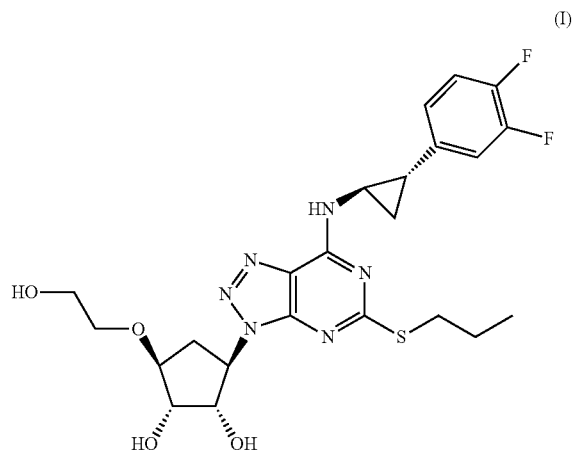

16 Claims, 13 Drawing Sheets

XRPD pattern of co-crystal of Compound A: gentisic acid Form A.

Note that diffractogram of this material evidences the presence of Compound A Polymorph II physical impurity as well as the co-crystal.

XRPD pattern of co-crystal of Compound A: gentisic acid Form B

Figure 3

XRPD pattern of co-crystal of Compound A: glutaric acid Form A.

Note that diffractogram of this material evidences the presence of glutaric acid physical impurity as well as the co-crystal.

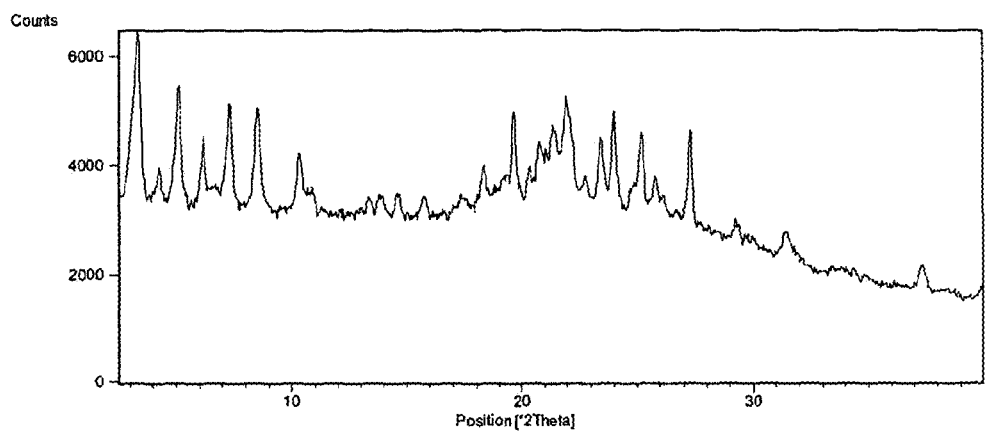

Figure 4

XRPD pattern of co-crystal of Compound A: glutaric acid Form B.

Note that diffractogram of this material evidences the presence of glutaric acid physical impurity as well as the co-crystal.

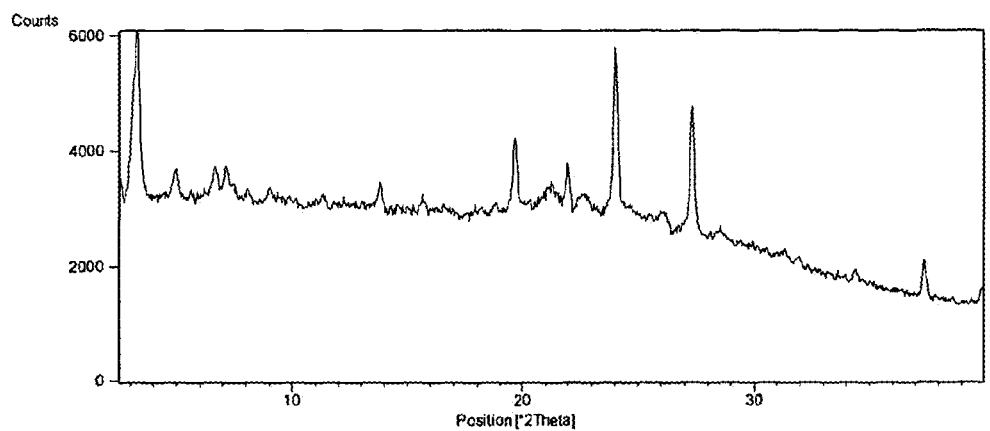

Figure 5

XRPD pattern of co-crystal of Compound A: glycolic acid Form A.

Note that diffractogram of this material evidences the presence of Compound A Polymorph II and glycolic acid physical impurities as well as the co-crystal.

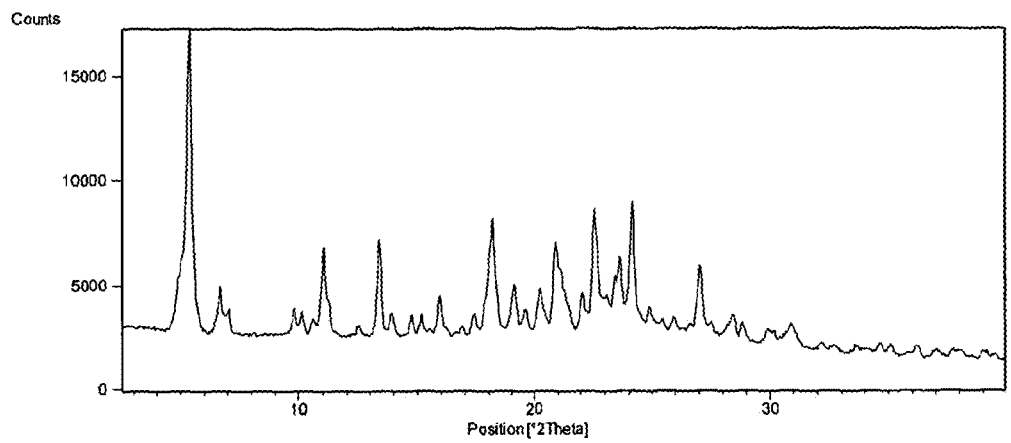

Figure 6

XRPD pattern of co-crystal of Compound A: salicylic acid Form A.

Note that diffractogram of this material evidences the presence of Compound A Polymorph II physical impurity as well as the co-crystal.

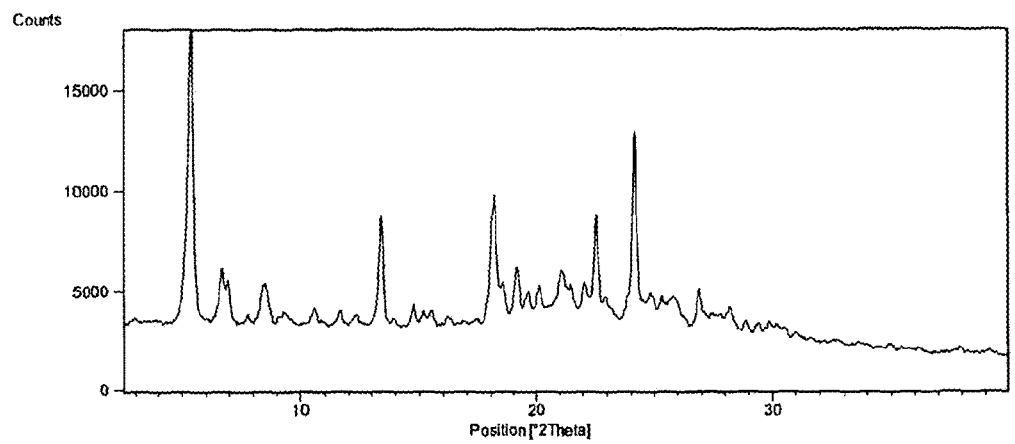

XRPD pattern of co-crystal of Compound A: salicylic acid Form B

XRPD pattern of co-crystal of Compound A: salicylic acid Form C

XRPD pattern of co-crystal of Compound A: malonic acid Form A

XRPD pattern of co-crystal of Compound A: maltol acid Form A.

Note that diffractogram of this material evidences the presence of Compound A Polymorph II physical impurity as well as the co-crystal.

Figure 11

XRPD pattern of co-crystal of Compound A: succinic acid Form A.

Note that diffractogram of this material evidences the presence of succinic acid physical impurity as well as the co-crystal.

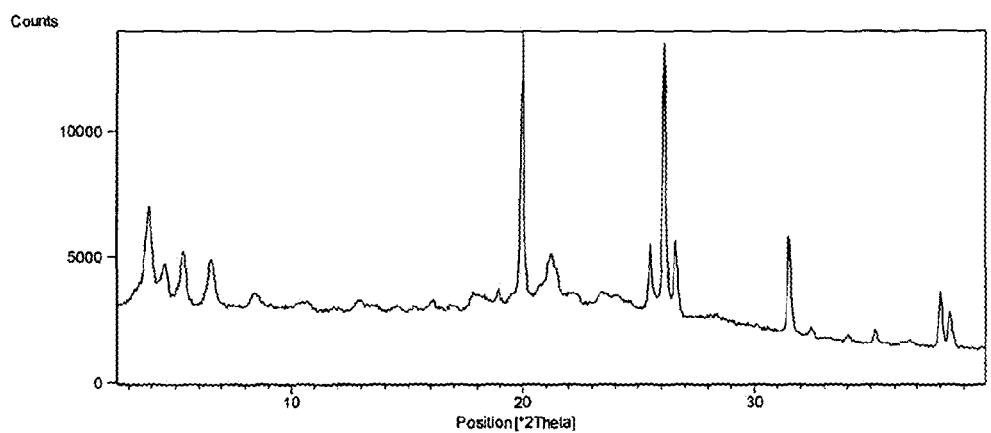

Figure 12

XRPD pattern of co-crystal of Compound A: succinic acid Form B.

Note that diffractogram of this material evidences the presence of succinic acid physical impurity as well as the co-crystal.

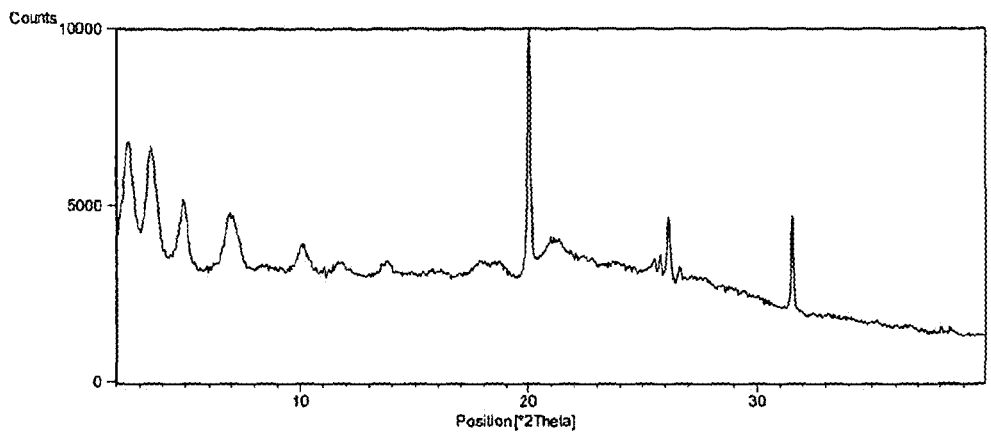

XRPD pattern of co-crystal of Compound A: vanillic acid Form A.

Note that the material contains co-crystal as well as Compound A Polymorph II physical impurity.

Infra-red spectrum of Compound A Form II

XRPD pattern of co-crystal of Compound A: malonic acid Form A.

Note that the material contains co-crystal as well as Compound A Polymorph II physical impurity.

Infra-red spectrum of co-crystal of Compound A: malonic acid

XRPD pattern of co-crystal of Form C of Compound A: succinic acid.

Note that diffractogram of this material evidences the presence of succinic acid physical impurity as well as the co-crystal.

Infra-red spectrum of co-crystal of Compound A: succinic acid.

Little free succinic acid present in this sample.

XRPD pattern of co-crystal of Compound A:decanoic acid Form A

Infra-red spectrum of co-crystal of Compound A: decanoic acid

XRPD pattern of co-crystal of Compound A: salicylic acid Form B.

Note that the material contains co-crystal as well as salicylic acid physical impurity.

Infra-red spectrum of co-crystal of Compound A: salicylic acid Form B

XRPD pattern of co-crystal of Compound A: gentisic acid Form C

Infra-red spectrum of co-crystal of the Compound A: gentisic acid Form C

Transmission / Wavenumber (cm-1)

XRPD pattern of co-crystal of Compound A: gentisic acid Form D

Key for all Figures: Compound A is {1S-[1α, 2α, 3β (1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol.

CO-CRYSTALS OF A TRIAZOLO [4,5-D] PYRIMIDE PLATELET AGGREGATION INHIBITOR

The present invention relates to novel co-crystals and more particularly to novel co-crystal forms of the compound of formula (I):

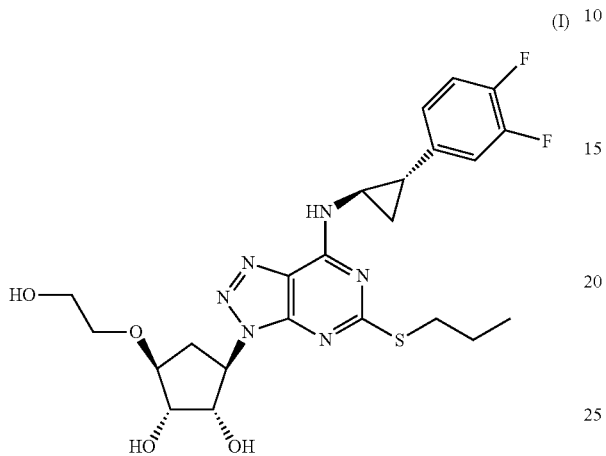

The compound of formula (I) is conventionally named: {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol, hereinafter named Compound A for convenience.

More specifically the invention relates to a number of co-crystals of Compound A, to processes for their preparation, to pharmaceutical compositions containing co-crystals of Compound A, to the use of co-crystals of Compound A in the manufacture of a medicament for use in the prevention of arterial thrombotic complications in patients with coronary artery, cerebrovascular or peripheral vascular disease and to methods of treating such diseases in the human or animal body by administering a therapeutically effective amount of a co-crystal of Compound A.

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty are also compromised by platelet-mediated occlusion or re-occlusion.

It has been found that adenosine 5'-diphosphate (ADP) acts as a key mediator of thrombosis. ADP-induced platelet aggregation is mediated by the $P_{2T}$ receptor subtype located on the platelet membrane. The $P_{2T}$ receptor (also known as $P2Y_{ADP}$ or $P2T_{AC}$) is primarily involved in mediating platelet aggregation/activation and is a G-protein coupled receptor which is as yet uncloned. The pharmacological characteristics of this receptor have been described, for example, in the references by Humphries et al., Br. J. Pharmacology (1994), 113, 1057-1063, and Fagura et al., Br. J. Pharmacology (1998) 124, 157-164. It has been shown that antagonists at this receptor offer significant improvements over other anti-thrombotic agents (see J. Med. Chem. (1999) 42, 213).

PCT International Patent Application WO 99/05143 discloses generically a series of triazolo[4,5-d]pyrimidine compounds having activity as $P_{2T}$ ($P2Y_{ADP}$ or $P2T_{AC}$) antagonists. Compound A is embraced by the generic scope of PCT International Patent Application WO 99/05143 but is not specifically disclosed therein.

Compound A exhibits high potency as a $P_{2T}$ ($P2Y_{ADP}$ or $P2T_{AC}$) antagonist and has a surprisingly high metabolic stability and bioavailability. Compound A is specifically exemplified in International Patent Application WO00/34283 and may exist in a number of different substantially crystalline forms referred to hereafter as Polymorph I, Polymorph II, Polymorph III and Polymorph IV as disclosed in PCT International Publication No. WO01/92262.

Alternative forms of compounds in the form of co-crystals can be useful for facilitating manufacturing and processing, for example of tablet forms and may also have potential for modulating properties such as solubility, dissolution, absorption, bioavailability and/or hygroscopicity over the free form.

It has now been found that Compound A can form co-crystal forms with a number of specific co-former molecules. Furthermore these co-crystals can exist in more than one crystallographically distinct forms, e.g. polymorphs, solvates, hydrates.

Accordingly, the present invention provides a co-crystal of the compound {1S-[1α, 2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol of formula (I) and a co-former molecule

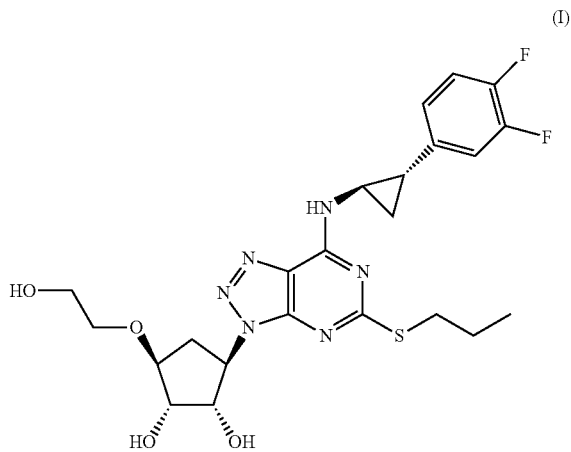 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

wherein the co-former molecule is selected from glycolic acid, salicylic acid, decanoic (capric) acid, gentisic acid (2,5-dihydroxybenzoic acid), glutaric acid, vanillic acid (4-hydroxy-3-methoxybenzoic acid), succinic acid, malonic acid or maltol (3-hydroxy-2-methyl-4-pyrone).

--BRIEF DESCRIPTION OF DRAWINGS

FIG. 3 shows an XRPD pattern of co-crystal of Compound A: glutaric acid Form A.

FIG. 4 shows an XRPD pattern of co-crystal of Compound A: glutaric acid Form B.

FIG. 5 shows an XRPD pattern of co-crystal of Compound A: glycolic acid Form A.

FIG. 6 shows an XRPD pattern of co-crystal of Compound A: salicylic acid Form A.

FIG. 11 shows an XRPD pattern of co-crystal of Compound A: succinic acid Form A.

FIG. 12 shows an XRPD pattern of co-crystal of Compound A: succinic acid Form B.

Figure 1:
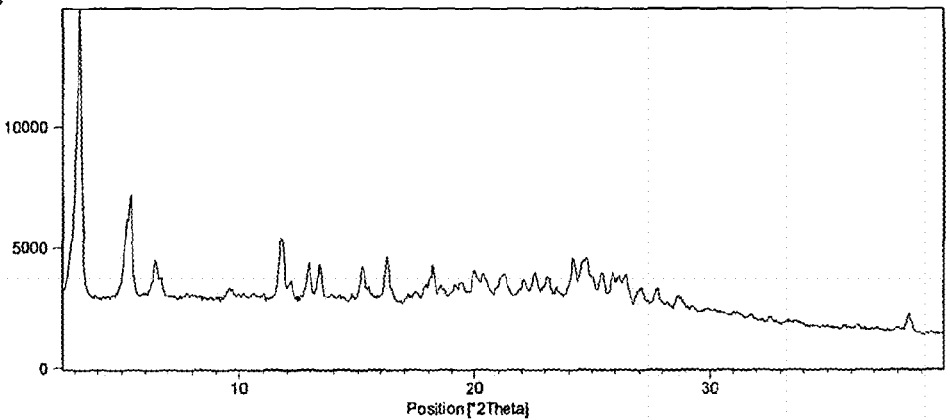
FIG. 1 shows an XRPD pattern of co-crystal of Compound A: gentisic acid Form A.

For the avoidance of doubt, the term co-crystal (or cocrystal) refers to a multicomponent system in which there exists a host API (active pharmaceutical ingredient) molecule or molecules and a guest (or co-former) molecule or molecules. In a co-crystal, both the API molecule and the guest (or co-former) molecule exist as a solid at room temperature when alone in their pure form (in order to distinguish the co-crystal from solvates or hydrates). Salts, in which significant or complete proton exchange occurs between the API molecule and the guest molecule, are excluded from this particular definition. In a co-crystal, the API and co-former molecules interact by hydrogen bonding and possibly other non-covalent interactions. It may be noted that a co-crystal may itself form solvates, including hydrates.

In particular embodiments of the invention, said co-crystal of the compound of Formula (I) with a co-former molecule is in a crystalline form selected from malonic acid co-crystal Form A, succinic acid co-crystal Form A, succinic acid co-crystal Form B, succinic acid co-crystal Form C, succinic acid co-crystal Form D, decanoic co-crystal Form A, salicylic acid co-crystal Form A, salicylic acid co-crystal Form B, salicylic acid co-crystal Form C, gentisic acid co-crystal Form A, gentisic acid co-crystal Form B, gentisic acid co-crystal Form C, gentisic acid co-crystal Form D, glutaric acid co-crystal Form A, vanillic acid co-crystal Form A, maltol co-crystal Form A or glycolic acid co-crystal Form A. It shall be noted that any one or more of these particular co-crystal forms may be disclaimed from any of the herein mentioned embodiments of the invention.

In a further aspect of the invention, said co-crystal of the compound of formula (I) is in a crystalline form having an XRPD pattern substantially as shown in any of the appended Figures.

According to the present invention there is provided a co-crystal of Compound A wherein said co-crystal is characterized by an X-ray powder diffraction pattern with specific peaks at about 2-theta (or d-spacing) as shown in Table 1-A.

TABLE 1-A

Primary Reflections distinguishing novel forms from pure Compound A free form or pure co-former solid forms

| Co-former | Co-crystal Form | Angle (° 2θ) (measured at 1.5418 Å; except salicylic acid Form B measured at 1.5406 Å) | d-spacing (Å) |
|---|---|---|---|
| Malonic acid | A | 6.12, 9.62, 12.25, 14.43, 18.16 | 14.4, 9.2, 7.2, 6.1, 4.88 |
| Succinic acid | A | 3.89, 4.53, 6.54 | 22.7, 19.5, 13.5 |
| Succinic acid | B | 2.49, 3.48, 4.88, 6.90 | 35.5, 25.4, 18.1, 12.8 |
| Succinic acid | C | 6.93, 7.74, 8.75, 14.09 | 12.7, 11.4, 10.1, 6.3, |
| Decanoic acid | A | 6.19, 9.28, 10.23, 16.47, 20.59 | 14.3, 9.5, 8.6, 5.4, 4.31 |
| Salicylic acid | A | 6.93, 8.47, 11.66, 12.33 | 12.7, 10.4, 7.6, 7.2 |
| Salicylic acid | B | 6.07, 8.03, 18.81, 20.50 | 14.6, 11.0, 4.71, 4.33 |
| Salicylic acid | C | 4.22, 7.37, 18.28 | 20.9, 12.0, 4.85 |
| Gentisic acid | A | 3.20, 11.80, 15.23, 16.28 | 27.6, 7.5, 5.8, 5.4 |
| Gentisic acid | B | 4.00, 6.90, 7.71, 10.11 | 22.1, 12.8, 11.5, 8.7 |
| Gentisic acid | C | 3.46, 4.84, 5.60, 10.16, 11.81, 20.99 | 25.5, 18.2, 15.8, 8.7, 7.5, 4.23 |
| Gentisic acid | D | 3.24, 6.3, 9.5, 12.0, 12.5 | 27.2, 13.9, 9.4, 7.4, 7.1 |
| Glutaric acid | A | 3.37, 4.27, 7.33, 8.53 | 26.2, 20.7, 12.1, 10.4 |
| Glutaric acid | B | 3.30, 4.96, 6.68, 7.14 | 26.7, 17.8, 13.2, 12.4 |
| Vanillic acid | A | 5.61, 9.64, 14.54, 20.10 | 15.7, 9.2, 6.1, 4.41 |
| Maltol | A | 3.13, 6.28, 8.35, 11.59 | 28.2, 14.1, 10.6, 7.6 |
| Glycolic acid | A | 7.02, 9.82, 10.15 | 12.6, 9.0, 8.7 |

According to another aspect of the present invention there is provided a co-crystal of Compound A wherein said co-crystal is characterized by an X-ray powder diffraction pattern with specific peaks (in addition to those in Table 1-A) at about 2-theta (or d-spacing) as shown in Table 2-A.

TABLE 2-A

Secondary Reflections distinguishing novel forms from pure Compound A free form or pure co-former solid forms

| Co-former | Co-crystal Form | Angle (° 2θ) (measured at 1.5418 Å; except salicylic acid Form B measured at 1.5406 Å) | d-spacing (Å) |
|---|---|---|---|
| Malonic acid | A | 21.07, 21.52, 25.75 | 4.21, 4.13, 3.46 |

TABLE 2-A-continued

Secondary Reflections distinguishing novel forms from pure Compound A free form or pure co-former solid forms

| Co-former | Co-crystal Form | Angle (° 2θ) (measured at 1.5418 Å; except salicylic acid Form B measured at 1.5406 Å) | d-spacing (Å) |
|---|---|---|---|
| Succinic acid | A | 5.35, 8.43, 12.96, 25.53, 26.62 | 16.5, 10.5, 6.8, 3.49, 3.35 |
| Succinic acid | B | 10.08, 11.71, 13.78 | 8.8, 7.6, 6.4 |
| Succinic acid | C | 9.24, 11.53, 12.20, 12.70, 18.98, 21.05 | 9.6, 7.7, 7.3, 7.0, 4.68, 4.22 |
| Decanoic acid | A | 8.18, 8.72, 10.71, 14.37, 14.89, 17.50 | 10.8, 10.1, 8.3, 6.2, 6.0, 5.1 |
| Salicylic acid | A | 7.74, 18.52 | 11.4, 4.79 |
| Salicylic acid | B | 4.19, 5.06, 14.02 | 21.1, 17.5, 6.3 |
| Salicylic acid | C | none | none |
| Gentisic acid | A | 6.45, 12.18, 12.96 | 13.7, 7.3, 6.8 |
| Gentisic acid | B | 12.17, 13.67, 14.46, 17.73, 23.29, 25.64 | 7.3, 6.5, 6.1, 5.0, 3.82, 3.47 |
| Gentisic acid | C | 6.82, 13.59, 17.52, 19.46, 20.37 | 13.0, 6.5, 5.1, 4.56, 4.36 |
| Gentisic acid | D | 3.68, 4.20, 15.4 | 24.0, 21.0, 5.8 |
| Glutaric acid | A | 5.13, 6.19, 10.35 | 17.2, 14.3, 8.5 |
| Glutaric acid | B | 24.04, 27.34 | 3.70, 3.26 |
| Vanillic acid | A | 2.78, 8.46, 10.80, 11.27, 12.51, 12.88 | 31.7, 10.5, 8.2, 7.8, 7.1, 6.9 |
| Maltol | A | 9.47, 16.59, 22.67 | 9.3, 5.3, 3.92 |
| Glycolic acid | A | 11.04, 15.94, 23.43 | 8.0, 5.6, 3.79 |

In Tables 1-A and 2-A, d-spacing values below 5 Å are quoted to 2 decimal places (margin of error typically +/−0.05 Å), values above 5 Å may be rounded to one decimal place (margin of error typically +/−0.5 Å) and wherein 2-theta values are +/−0.2°.

In another aspect there is provided a crystalline form of co-crystal of the compound of formula (I) wherein each of said co-crystals is characterised in that it has an X-ray powder diffraction pattern with peaks as shown in Table 1-B.

TABLE 1-B

| Co-former | Co-crystal Form | Angle (° 2θ) (measured at 1.5418 Å; except salicylic acid Form B measured at 1.5406 Å) |
|---|---|---|
| Malonic acid | A | 6.1, 9.6, 12.3, 14.4, 18.2 |
| Succinic acid | A | 3.9, 4.5, 6.5 |
| Succinic acid | B | 2.5, 3.5, 4.9, 6.9 |
| Succinic acid | C | 6.9, 7.7, 8.8, 14.1 |
| Decanoic acid | A | 6.2, 9.3, 10.2, 16.5, 20.6 |
| Salicylic acid | A | 6.9, 8.5, 11.7, 12.3 |
| Salicylic acid | B | 6.1, 8.0, 18.8, 20.5 |
| Salicylic acid | C | 4.2, 7.4, 18.3 |
| Gentisic acid | A | 3.2, 11.8, 15.2, 16.3 |
| Gentisic acid | B | 4.0, 6.9, 7.7, 10.1 |
| Gentisic acid | C | 3.5, 4.8, 5.6, 10.2, 11.8, 21.0 |
| Gentisic acid | D | 3.2, 6.3, 9.5, 12.0, 12.5 |
| Glutaric acid | A | 3.4, 4.3, 7.3, 8.5 |
| Glutaric acid | B | 3.3, 5.0, 6.7, 7.1 |
| Vanillic acid | A | 5.6, 9.6, 14.5, 20.1 |
| Maltol | A | 3.1, 6.3, 8.4, 11.6 |
| Glycolic acid | A | 7.0, 9.8, 10.2 | wherein 2-theta values are +/−0.2°.

In another aspect there is provided a crystalline form of co-crystal of the compound of formula (I), wherein each of said co-crystals is characterised in that it has an X-ray powder diffraction pattern with peaks in addition to those in Table 1-B as shown in the following Table 2-B.

TABLE 2-B

| Co-former | Co-crystal Form | Angle (° 2θ) (measured at 1.5418 Å; except salicylic acid Form B measured at 1.5406 Å) |
|---|---|---|
| Malonic acid | A | 21.1, 21.5, 25.8 |
| Succinic acid | A | 5.4, 8.4, 13.0, 25.5, 26.6 |
| Succinic acid | B | 10.1, 11.7, 13.8 |
| Succinic acid | C | 9.2, 11.5, 12.2, 12.7, 19.0, 21.1 |
| Decanoic acid | A | 8.2, 8.7, 10.7, 14.4, 14.9, 17.5 |
| Salicylic acid | A | 7.7, 18.5 |
| Salicylic acid | B | 4.2, 5.1, 14.0 |
| Gentisic acid | A | 6.5, 12.2, 13.0 |
| Gentisic acid | B | 12.2, 13.7, 14.5, 17.7, 23.3, 25.6 |
| Gentisic acid | C | 6.8, 13.6, 17.5, 19.5, 20.4 |
| Gentisic acid | D | 3.7, 4.2, 15.4 |
| Glutaric acid | A | 5.1, 6.2, 10.4 |
| Glutaric acid | B | 24.0, 27.3 |
| Vanillic acid | A | 2.8, 8.5, 10.8, 11.3, 12.5, 12.9 |
| Maltol | A | 9.5, 16.6, 22.7 |
| Glycolic acid | A | 11.0, 16.0, 23.4 | wherein 2-theta values are +/−0.2°.

Particular co-crystals of the invention are those of Compound A with malonic (Form A) and gentisic (Form D) co-former molecules, which have an improved solubility profile compared to free form compound A Polymorph II (see WO 01/92262), see Example 4 herein, and which may allow faster absorption of Compound A and/or alternative formulation options.

In a specific embodiment of the invention, different stoichiometries of pure co-crystals of the invention are possible, e.g. 1:1, 1:2 etc. or 1:1, 1:2 etc. (Compound A API:co-former or co-former:Compound A API).

Co-crystals of the invention may exist in amorphous form or in a range of crystalline forms.

When a co-crystal according to the invention is referred to herein as being (substantially) crystalline, this is, for example, greater than about 60% crystalline, such as greater than about 80%, particularly greater than about 90%, more particularly greater than about 95%, wherein the % crystallinity refers to the % by weight of the total sample mass of co-crystal which is crystalline.

In a further specific embodiment of the invention, a co-crystal of the compound of formula (I), in any of the crystalline forms disclosed herein, is in substantially crystalline form, for example, a co-crystal as defined herein wherein 80%, 90% or, more particularly, 95% of the co-crystal is in crystalline form.

In a further specific embodiment of the invention, a co-crystal of the compound of formula (I), in any of the crystalline forms defined herein, is a form substantially free from other forms of the compound of formula (I) and/or substantially free from excess co-former molecule; for example, a form comprising less than 10 wt. %, 5 wt. %, 3 wt. % or, more particularly, less than 1 wt. % of excess co-former and/or Compound A API molecule.

In preparing co-crystals of Compound A with the co-former molecules defined herein, a range of API:co-former molar ratios/stoichiometries may be achieved, for example an overall API:co-former molar ratio of 1:1.1 reflecting a mixture of Compound A API:co-former co-crystal and a 0.1 molar excess of co-former molecule. Any molar ratio/stoichiometry containing a Compound A:co-former co-crystal as defined herein is within the scope of this invention.

Mixtures comprising Compound A:co-former co-crystal as defined herein with free co-former molecule and/or free Compound API molecule are within the scope of this invention; for example, mixtures between 50 wt. % and 90 wt. % of Compound A:co-former co-crystal and the remainder is co-former molecule in free form and/or Compound A in free form.

Thus, in one aspect, the present invention relates to a solid comprising a mixture of:

a) a co-crystal of the compound of formula (I) and a co-former molecule selected from glycolic acid, salicylic acid, decanoic (capric) acid, gentisic acid (2,5-dihydroxybenzoic acid), glutaric acid, vanillic acid (4-hydroxy-3-methoxybenzoic acid), succinic acid, malonic acid or maltol (3-hydroxy-2-methyl-4-pyrone), and b) said co-former molecule.

Said solid may comprise, for instance, (a) 80-90 wt. % of said co-crystal of the compound of formula (I) as defined herein, and (b) 10-20 wt. % of said co-former molecule.

In a further aspect, the present invention relates to a solid of the compound of formula (I) as defined herein, said solid comprising a mixture of:

a) a co-crystal, in particular a crystalline co-crystal, of the compound of formula (I) and a co-former molecule selected from glycolic acid, salicylic acid, decanoic (capric) acid, gentisic acid (2,5-dihydroxybenzoic acid), glutaric acid, vanillic acid (4-hydroxy-3-methoxybenzoic acid), succinic acid, malonic acid or maltol (3-hydroxy-2-methyl-4-pyrone), and b) Polymorph I and/or Polymorph II and/or Polymorph III and/or Polymorph IV of the compound of formula (I).

In a further aspect, a mixture of (a) a co-crystal of the compound of formula (I) as defined herein with (b) Polymorph I and/or Polymorph II and/or Polymorph III and/or Polymorph IV of the compound of formula (I) comprises a (wt. %) mixture of 80%-90% co-crystal with 10%-20% Polymorph I and/or Polymorph II and/or Polymorph III and/or Polymorph IV of the compound of formula (I).

In a further aspect of the invention, there is provided a co-crystal obtainable by any of the processes or Examples mentioned herein.

A co-crystal of Compound A as defined herein is believed to liberate (in-vivo) Compound A which acts as a $P_{2T}$ ($P2Y_{ADP}$ or $P2T_{AC}$) receptor antagonist. Accordingly, a co-crystal of Compound A as defined herein is useful in therapy, including combination therapy with simultaneous, sequential or separate administration of at least one other pharmacologically active agent. In particular, a co-crystal of Compound A as defined herein is indicated for use in the treatment or prophylaxis of arterial thrombotic complications in patients with coronary artery, cerebrovascular or peripheral vascular disease. Arterial thrombotic complications may include unstable angina, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, including coronary angioplasty (PTCA), endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

According to a further aspect of the present invention there is provided a co-crystal of Compound A as defined herein for use in a method of treatment of the human or animal body by therapy.

According to an additional feature of the present invention there is provided a co-crystal of Compound A as defined herein for use as a medicament. Particularly, a co-crystal of Compound A as defined herein is used as a medicament to antagonise the $P_{2T}$ ($P2Y_{ADP}$ or $P2T_{AC}$) receptor in a warm-blooded animal such as a human being. More particularly, a co-crystal of Compound A as defined herein is used as a medicament for treating or preventing arterial thrombotic complications in patients with coronary artery, cerebrovascular or peripheral vascular disease in a warm-blooded animal such as a human being.

According to the invention there is further provided the use of a co-crystal of Compound A as defined herein in the manufacture of a medicament for use as an antagonist of the $P_{2T}$ ($P2Y_{ADP}$ or $P2T_{AC}$) receptor. In particular there is further provided the use of a co-crystal of Compound A as defined herein in the manufacture of a medicament for use in the treatment or prevention of arterial thrombotic complications in patients with coronary artery, cerebrovascular or peripheral vascular disease.

The invention also provides a method of treatment or prevention of arterial thrombotic complications in patients with coronary artery, cerebrovascular or peripheral vascular disease, which comprises administering to a person suffering from or susceptible to such a disorder a therapeutically effective amount of a co-crystal of Compound A as defined herein.

A co-crystal of Compound A as defined herein may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

A co-crystal of Compound A as defined herein may be administered on its own or as a pharmaceutical composition comprising a co-crystal of Compound A as defined herein in combination with a pharmaceutically acceptable diluent, adjuvant and/or carrier. Therefore there is provided as a further feature of the invention a pharmaceutical composition comprising a co-crystal of Compound A as defined herein in association with a pharmaceutically acceptable diluent, adjuvant and/or carrier. Particularly preferred are compositions not containing material capable of causing an adverse reaction, such as an adverse allergic reaction.

Dry powder formulations and pressurised HFA aerosols of a co-crystal of Compound A as defined herein may be administered by oral or nasal inhalation. For inhalation a co-crystal of Compound A as defined herein is desirably finely divided. A co-crystal of Compound A as defined herein may also be administered by means of a dry powder inhaler. The inhaler may be a single or a multi dose inhaler, and may be a breath actuated dry powder inhaler.

One possibility is to mix the finely divided co-crystal of Compound A as defined herein with a carrier substance, e.g. a mono-, di- or polysaccharide, a sugar alcohol or another polyol. Suitable carriers include sugars and starch. Alternatively the finely divided co-crystal of Compound A as defined herein may be coated by another substance. The powder mixture may also be dispensed into hard gelatine capsules, each containing the desired dose of a co-crystal of Compound A as defined herein.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system a co-crystal of Compound A as defined herein with or without a carrier substance is delivered to the patient.

The pharmaceutical composition comprising a co-crystal of Compound A as defined herein may conveniently be tablets, pills, capsules, syrups, powders or granules for oral administration; sterile parenteral or subcutaneous solutions, suspensions for parenteral administration or suppositories for rectal administration.

For oral administration a co-crystal of Compound A as defined herein may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, a co-crystal of Compound A as defined herein may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing a co-crystal of Compound A as defined herein, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

A co-crystal of Compound A as defined herein is believed to liberate Compound A which acts as a $P_{2T}$ ($P2Y_{ADP}$ or $P2T_{AC}$) receptor antagonist as disclosed in International Patent Application No. WO 00/34283. The pharmacological properties of Compound A and co-crystals thereof described herein may be assessed, for example, using one or more of the procedures set out in International Patent Application No. WO 00/34283. For example, the preparation for the assay of the $P_{2T}$ ($P2Y_{ADP}$ or $P2T_{AC}$) receptor agonist/antagonist activity in washed human platelets is set out in International Patent Application No. WO 00/34283 wherein antagonist potency is estimated as a % inhibition of the control ADP response to obtain an $IC_{50}$. In WO 00/34283 compounds exemplified therein are reported to have $pIC_{50}$ values of more than 5.0.

EXAMPLES

The invention is illustrated herein by means of the following non-limiting Examples, data and Figures in which, unless otherwise stated:
(i) yields are given for illustration only and are not necessarily the maximum attainable;
(ii) where product is used for seeding it can be obtained by prior known or disclosed processes.

Standard analysis techniques that can be used include XRPD, FTIR to help characterise H-bonding, solid-state NMR, solution state NMR, DSC and TGA.

X-Ray Powder Diffraction

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used so that the intensities in the XRPD traces included herein are illustrative and not intended to be used for absolute comparison.

The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996).

It is also stated above that, in general, a measurement error of a diffraction angle in an X-ray powder diffractogram is about 2-theta=0.5° or less (or, more suitably, about 2-theta=0.2° or less) and such degree of a measurement error should be taken into account when considering the X-ray powder diffraction patterns, and when interpreting the peak positions referred to in the text above and in the Tables herein. D-spacing values below 5 Å are quoted to 2 decimal places (margin of error typically +/−0.05 Å), values above 5 Å may be rounded to one decimal place (margin of error typically +/−0.5 Å) and wherein 2-theta values are +/−0.2°.

Example 1

Compound A Co-crystal Formation

The following co-formers, which are readily available materials, were used in experiments with Compound A (which can be prepared as described in the PCT applications mentioned herein—the relevant contents of which are incorporated herein by reference).

Glycolic acid:

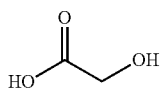

Salicylic acid:

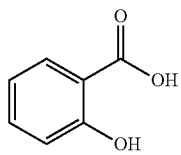

Decanoic (capric) acid:

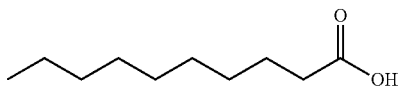

Gentisic acid (2,5-dihydroxybenzoic acid):

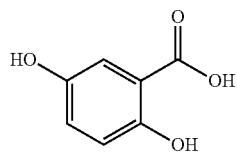 [SMILES: O=C(O)c1cc(O)ccc1O]

Glutaric acid:

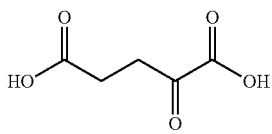

Vanillic acid (4-hydroxy-3-methoxybenzoic acid)

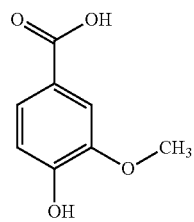

Succinic acid:

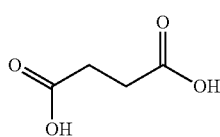

Malonic acid:

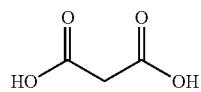

Maltol (3-hydroxy-2-methyl-4-pyrone):

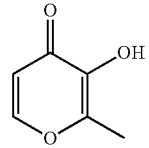

X-ray powder diffraction (XRPD) analyses were performed using an Inel XRG-3000 diffractometer equipped with a CPS (Curved Position Sensitive) detector with a 2θ range of 120°. Real time data were collected using Cu—Kα radiation (wavelength of X-rays 1.5418 Å) at a resolution of 0.03° 2θ. The tube voltage and amperage were set to 40 kV and 30 mA, respectively. The monochromator slit was set at 5 mm by 160 μm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 5 min. Instrument calibration was performed using a silicon reference standard.

Example 1-A

Compound A: Decanoic Acid Co-crystal Form A 10.3 mg decanoic acid in 500 μL of methanol was added to 2 mL of a filtered solution of Compound A in acetone (15 mg/mL) with stirring. The vial was capped and wrapped in parafilm.

Figure 19:
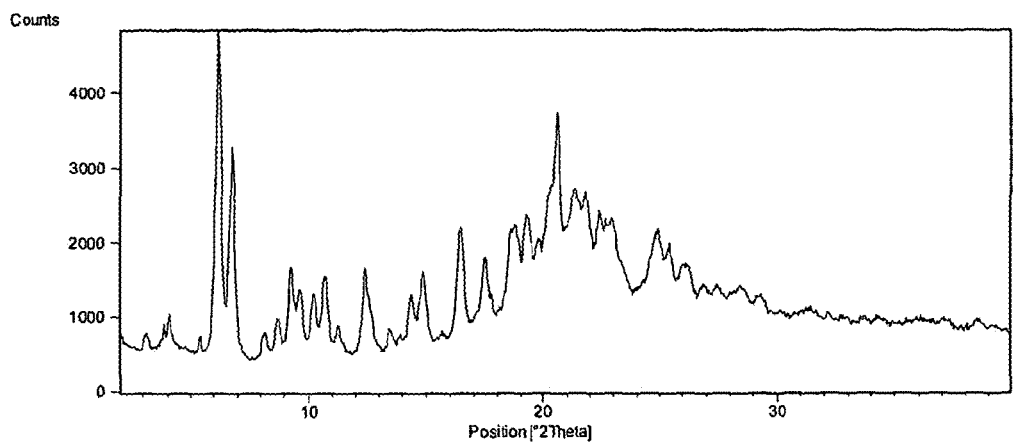
FIG. 19 shows an XRPD pattern of co-crystal of Compound A: decanoic acid Form A.

The resulting co-crystal material gave a diffractogram consistent with peaks listed in Example 2-C (see FIG. 19).

Example 1-B

Compound A: Gentisic Acid Co-crystal Forms A and B 8.7 mg gentisic acid in 500 μL of acetone was added to 2 mL of a filtered solution of Compound A in acetone (15 mg/mL) with stirring. The vial was capped and wrapped in parafilm.

The resulting material was denoted Form A, the diffractogram shown in FIG. 1. Note that diffractogram of this material evidences the presence of Compound A Polymorph II as a physical impurity as well as the co-crystal.

7.2 mg gentisic acid in 300 μL of methanol was added to 3 mL of a filtered solution of Compound A in dichloromethane (8 mg/mL) with stirring. The vial was capped and wrapped in parafilm.

Figure 2:
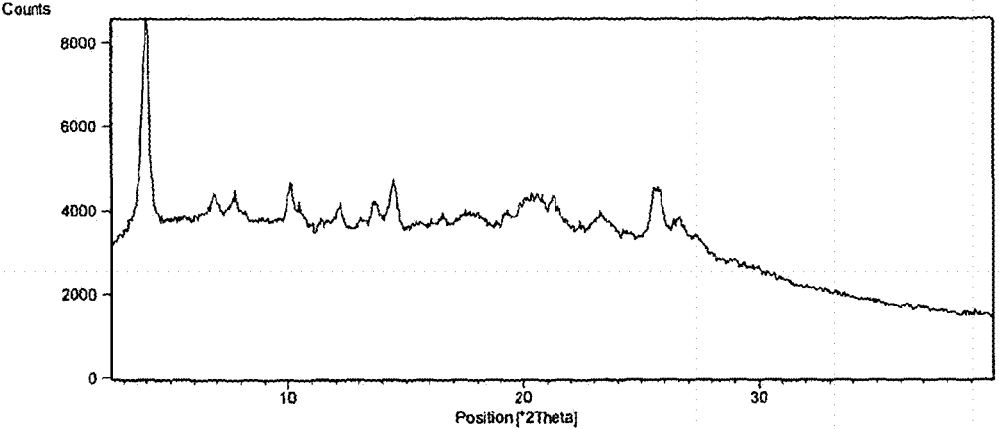
FIG. 2 shows an XRPD pattern of co-crystal of Compound A: gentisic acid Form B.

The resulting co-crystal material was denoted Form B, the diffractogram shown in FIG. 2.

Example 1-C

Compound A: Glutaric Acid Co-crystal Forms A and B 80.6 mg of Compound A was ground for 2 minutes with 19.8 mg of glutaric acid, in the presence of 70 mL of acetonitrile.

The resulting co-crystal material was denoted Form A, the diffractogram shown in FIG. 3. Note that diffractogram of this material evidences the presence of glutaric acid as a physical impurity as well as the co-crystal.

30 mg of Compound A was added to 2 mL of a filtered solution of glutaric acid in diethyl ether (30 mg/mL) with stirring and shaken for 8 days. The vial was capped and wrapped in parafilm.

The resulting co-crystal material was denoted Form B, the diffractogram shown in FIG. 4. Note that diffractogram of this material evidences the presence of glutaric acid physical impurity as well as the co-crystal.

Example 1-D

Compound A: Glycolic Acid Co-crystal Form A 86.4 mg of Compound A was ground for 2 minutes with 13 mg of glycolic acid, in the presence of 70 mL of acetonitrile.

The resulting co-crystal material was denoted Form A, the diffractogram shown in FIG. 5. Note that diffractogram of this material evidences the presence of Compound A Polymorph II and glycolic acid as physical impurities as well as the co-crystal.

Example 1-E

Compound A: Salicylic Acid Co-crystal Forms A, B and C 103 mg of Compound A was ground for 2 minutes with 26 mg of salicylic acid, in the presence of 70 µL of acetonitrile. The sample dried on grinding, and the sample transferred to a clean vial together with an additional 50 µL of acetonitrile.

The resulting co-crystal material was denoted Form A, the diffractogram shown in FIG. 6. Note that diffractogram of this material evidences the presence of Compound A Polymorph II as a physical impurity as well as the co-crystal.

A solution of 8 mg of salicylic acid in 500 mL acetone was added to 2 mL of a filtered solution of Compound A in acetone (15 mg/mL) with stirring. The vial was capped and wrapped in parafilm.

Figure 7:
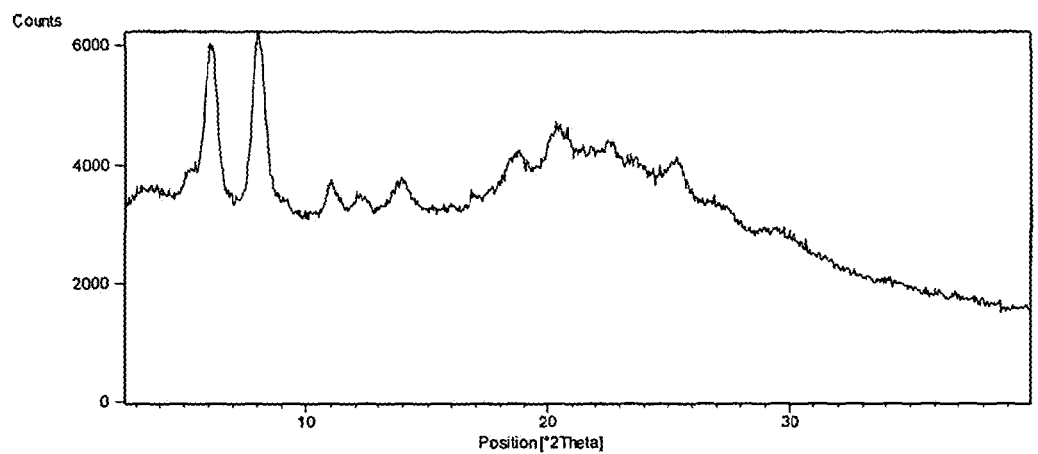
FIG. 7 shows an XRPD pattern of co-crystal of Compound A: salicylic acid Form B.

The resulting co-crystal material was denoted Form B, the diffractogram shown in FIG. 7 consistent with peaks listed in Example 2-D.

6.5 mg salicylic acid in 300 µL of methanol was added to 3 mL of a filtered solution of Compound A in dichloromethane (8 mg/mL) with stirring. The vial was capped and wrapped in parafilm.

Figure 8:
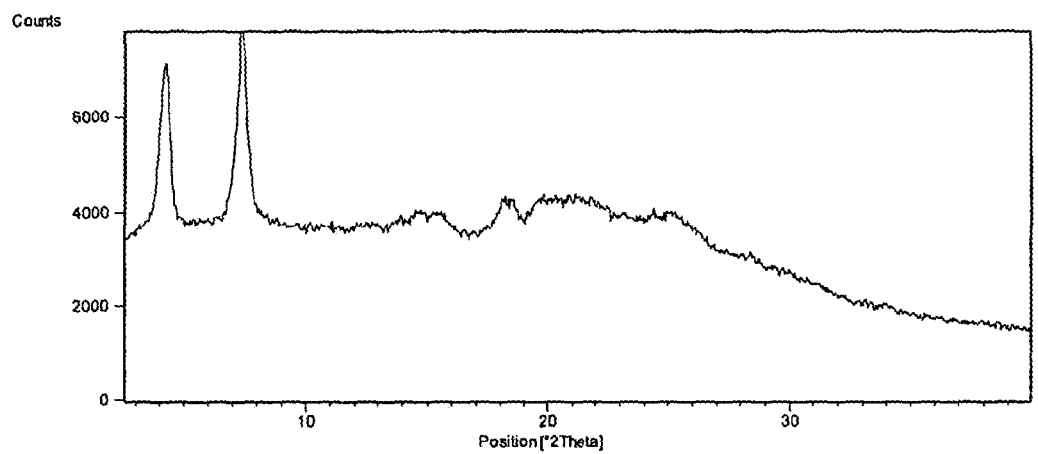
FIG. 8 shows an XRPD pattern of co-crystal of Compound A: salicylic acid Form C.

The resulting co-crystal material was denoted Form C, the diffractogram shown in FIG. 8.

Example 1-F

Compound A: Malonic Acid Co-crystal Form A 72 mg of Compound A was ground for 2 minutes with 15 mg of glutaric acid, in the presence of 70 mL of acetonitrile.

Figure 9:
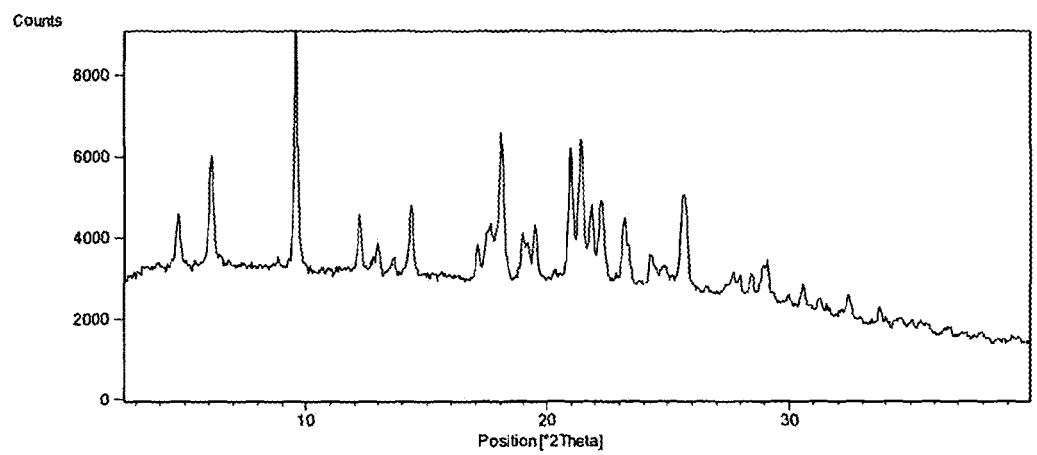
FIG. 9 shows an XRPD pattern of co-crystal of Compound A: malonic acid Form A.

The resulting co-crystal material gave a diffractogram FIG. 9 consistent with peaks listed in Example 2-A (see FIG. 15) but with no evidence of any Compound A Polymorph II as a physical impurity.

In a further method, 6 mg malonic acid in 500 µL of acetone was added to 2 mL of a filtered solution of Compound A in acetone (15 mg/mL) with stirring. The vial was capped and wrapped in parafilm.

Figure 15:
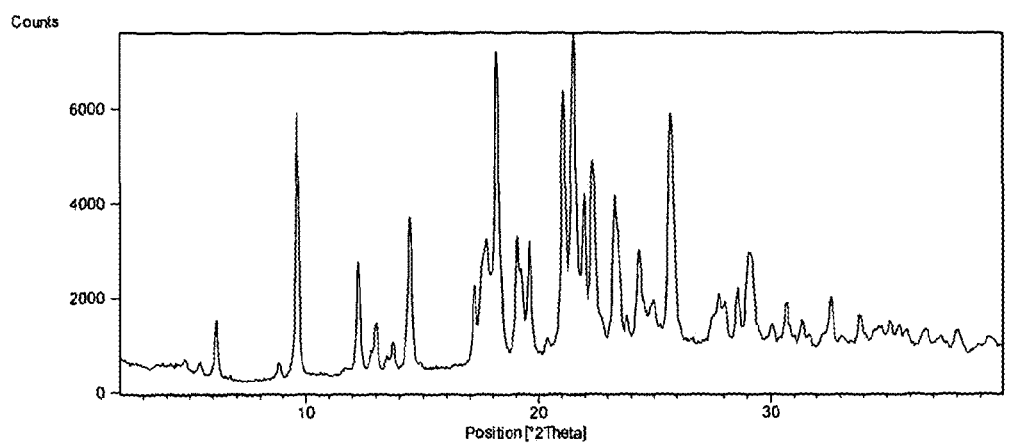
FIG. 15 shows an XRPD pattern of co-crystal of Compound A: malonic acid Form A.

The resulting co-crystal material gave a diffractogram consistent with peaks listed in Example 2-A (see FIG. 15). Note that diffractogram of this material evidences the presence of Compound A Polymorph II as a physical impurity as well as the co-crystal.

In a further method, 4.8 mg malonic acid in 300 µL of methanol was added to 3 mL of a filtered solution of Compound A in dichloromethane (8 mg/mL) with stirring. The vial was capped and wrapped in parafilm.

The resulting co-crystal material gave a diffractogram consistent with peaks listed in Example 2-A (see FIG. 15). Note that diffractogram of this material evidences the presence of Compound A Polymorph II as a physical impurity as well as the co-crystal.

Example 1-G

Compound A: Maltol Acid Co-crystal Form A 7.3 mg maltol acid in 500 µL of methanol was added to 2 mL of a filtered solution of Compound A in acetone (15 mg/mL) with stirring. The vial was capped and wrapped in parafilm.

Figure 10:
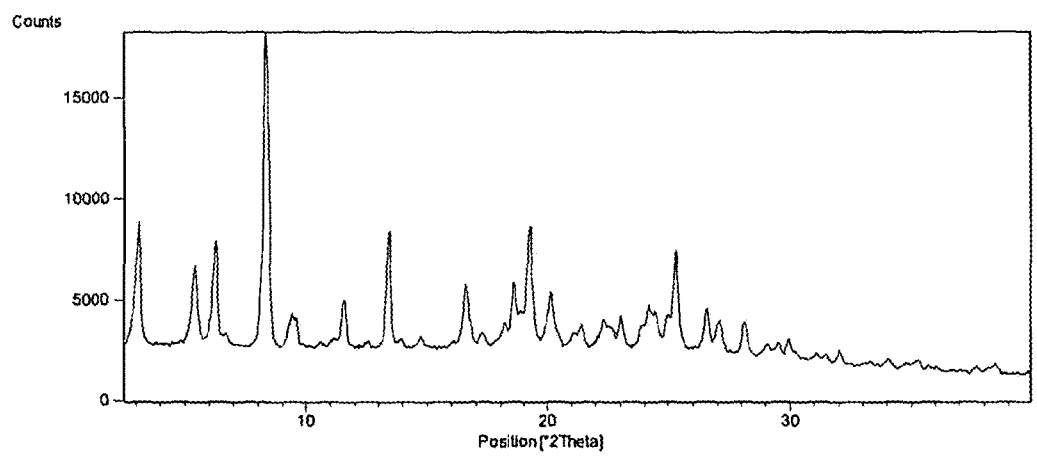
FIG. 10 shows an XRPD pattern of co-crystal of Compound A: maltol acid Form A.

The resulting co-crystal material was denoted Form A, the diffractogram shown in FIG. 10. Note that diffractogram of this material evidences the presence of Compound A Polymorph II as a physical impurity as well as the co-crystal.

Example 1-H

Compound A: Succinic Acid Acid Co-crystal Forms A and B 13.6 mg succinic acid was added to 1.5 mL of a filtered solution made from 301 mg Compound A in 15 mL of ethyl acetate. The resulting solution was evaporated to give solids (evaporation was terminated prior to dryness).

The resulting co-crystal material was denoted Form A, the diffractogram shown in FIG. 11. Note that diffractogram of this material evidences the presence of succinic acid as a physical impurity as well as the co-crystal.

72 mg of Compound A was ground for 2 minutes with 16 mg of succinic acid, in the presence of 70 µL of acetonitrile. The resultant material was transferred to a clean vial and 70 µL of acetonitrile added. The vial was capped and sealed with parafilm.

The resulting co-crystal material was denoted Form B, the diffractogram shown in FIG. 12. Note that diffractogram of this material evidences the presence of succinic acid as a physical impurity as well as the co-crystal.

Example 1-I

Compound A: Vanillic Acid Acid Co-crystal Form A 9.9 mg vanillic acid in 500 µL of methanol was added to 2 mL of a filtered solution of Compound A in acetone (15 mg/mL) with stirring. The vial was capped and wrapped in parafilm.

Figure 13:
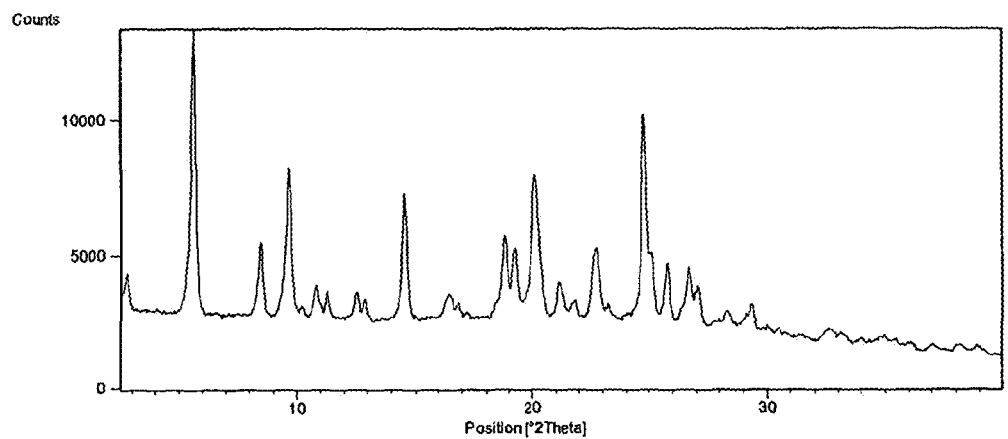
FIG. 13 shows an XRPD pattern of co-crystal of Compound A: vanillic acid Form A.

The resulting co-crystal material was denoted Form A, the diffractogram shown in FIG. 13. Note that the material contains co-crystal as well as Compound A Polymorph II physical impurity.

Example 2

Further Assessment of Compound A Co-crystal Formation

The following experiments were performed with Compound A co-crystals.

X-Ray Powder Diffraction (XRPD) patterns were collected under the following conditions:

Powder X-ray diffraction was recorded with a θ-θ Philips X'Pert PRO (wavelength of X-rays 1.5418 Å Cu source, Voltage 45 kV, filament emission 40 mA). Samples were scanned from 2-40° 2θ using a 0.033° step width and a 200 second count time using an X'celerator detector (active length 2.13° 2θ).

In the case of Example 2-D, Powder X-ray diffraction was recorded with a θ-2θ Philips X'Pert PRO (wavelength of X-rays 1.5406 Å Cu source, Voltage 45 kV, filament emission 40 mA). Samples were scanned from 2-40° 2θ using a 0.033° step width and a 200 second count time using an X'celerator detector (active length 2.13° 2θ).

In the case of Example 2-E, Powder X-ray diffraction was recorded with a θ-θ PANalytical CUBIX (wavelength of X-rays 1.5418 Å Cu source, Voltage 45 kV, filament emission 40 mA). Samples were scanned from 2-40° 2θ using a 0.02° step width and a 100 second count time using an X'celerator detector (active length 2.55° 2θ).

Infra-red spectra were collected on a golden gate ATR attachment on a Nicolet 6700 infrared spectrometer. Data was collected with 32 scans under a torque pressure of 20 cNm, using a resolution of 2 $cm^{-1}$.

It will be understood that relative intensities of infra-red peaks may vary according the sampling technique implemented.

For reference, Compound A preparation and XRPD patterns have been previously disclosed in PCT International Patent Application No. PCT/SE01/01239 (Publication No. WO01/92262).

Figure 14:
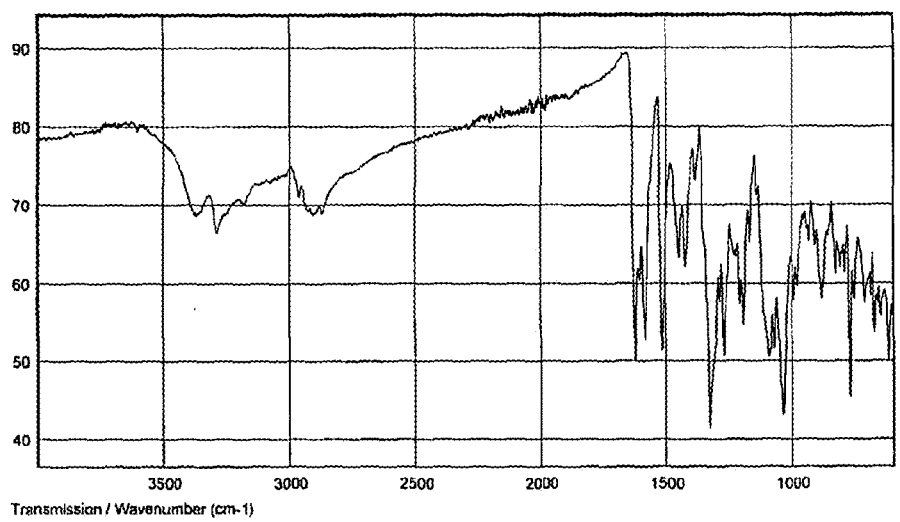
FIG. 14 shows infra-red spectrum of Compound A Form II.

For reference, infra-red spectroscopy of Compound A Polymorph II, exhibits distinguishing peaks at 3373, 3289, 3248, 3177, 2962, 2924, 2907, 2871, 1624, 1604, 1583 and 1517 $cm^{-1}$ (see FIG. 14).

Example 2-A

Compound A: Malonic Acid Co-crystal Form A 50 mg of Compound A Polymorph II were ground for 2-3 minutes with a 1:1 molar equivalent of malonic acid (11 mg), in the presence of approximately 30 microliters of acetonitrile. The resulting solid was analysed by XRPD and Infra-red spectroscopy.

XRPD of the sample gave rise to diffraction pattern, consistent with FIG. 9, having intense reflections due to the co-crystal at 14.43, 9.19, 7.22, 6.13 and 4.88 and more specifically, 14.43, 9.19, 7.22, 6.13, 4.88, 4.21, 4.13 and 3.46 Å.

FIG. 15 shows the XRPD pattern of Form A of the Compound A: malonic acid co-crystal. Note that the material contains co-crystal as well as Compound A Polymorph II as a physical impurity.

Figure 16:
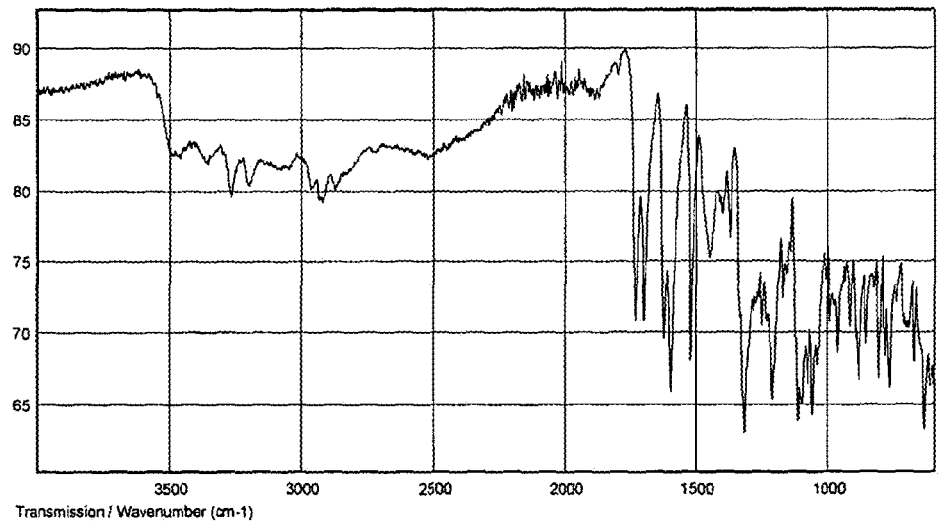
FIG. 16 shows infra-red spectrum of co-crystal of Compound A: malonic acid.

Infra-red spectroscopy data indicates presence of bands due to both Compound A and co-crystal former, but shifted (FIG. 16). The shift in the positions of the peaks, particularly in the region of hydrogen bonding shows the form is not a simple physical mixture and is highly indicative of co-crystal formation. It should be noted that not all peaks are shifted, only those impacted by the change in interaction as a result of co-crystal formation. Peaks specific to the co-crystal include 3268 (a), 3196 (a), 1730 (m), 1596 (a) $cm^{-1}$ and more preferably also include 1401, 1375, 1337, 1322, 1254, 1232, 1212, 1204, 1173, 1161, 1144, 1114, 1099, 1080, 1061, 1043, 1010 $cm^{-1}$ (where (m) and (a) peaks are unshifted with respect to m=malonic acid and a=Compound A peaks).

Example 2-B

Compound A: Succinic Acid Co-crystal Form C

A saturated solution of succinic acid was produced by saturating methanol with succinic acid and filtering. Compound A was added to 1 mL of this saturated solution to form a light suspension. The suspension was stirred over 7 days at ambient temperature, adding more Compound A if dissolution had occurred. After 7 days, stirring was terminated. Two solid materials were identified with different appearances. One material was identified as predominantly succinic acid by infrared spectroscopy. The other material was analysed by XRPD and Infra-red spectroscopy.

XRPD of the sample gave rise to a diffraction pattern, with intense reflections due to the co-crystal at 12.75, 11.43, 10.10, 6.29, 4.22 Å and more preferably, 12.75, 11.43, 10.10, 9.57, 7.67, 7.26, 6.97, 6.29, 4.68 and 4.22 Å.

Figure 17:
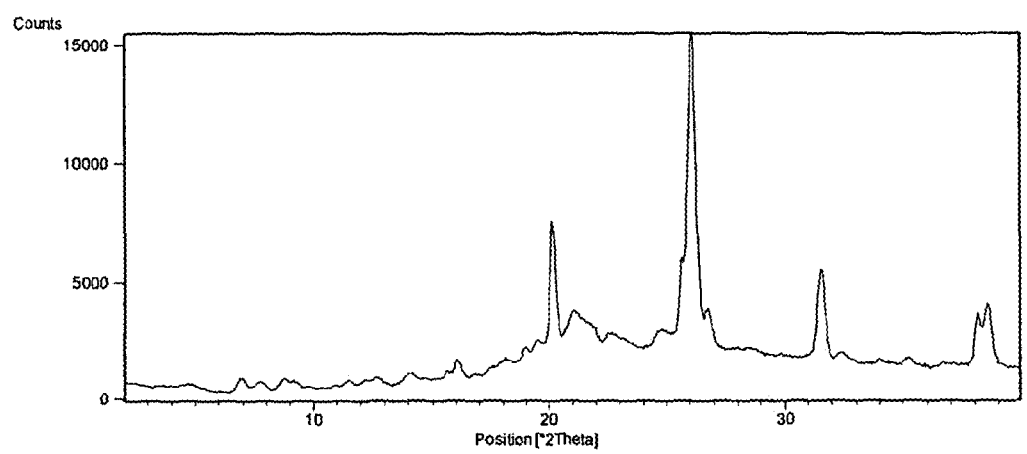
FIG. 17 shows an XRPD pattern of co-crystal of Form C of Compound A: succinic acid.

FIG. 17 shows the XRPD pattern of Form A of the Compound A: succinic acid co-crystal. Note that diffractogram of this material evidences the presence of succinic acid as a physical impurity as well as the co-crystal.

Figure 18:
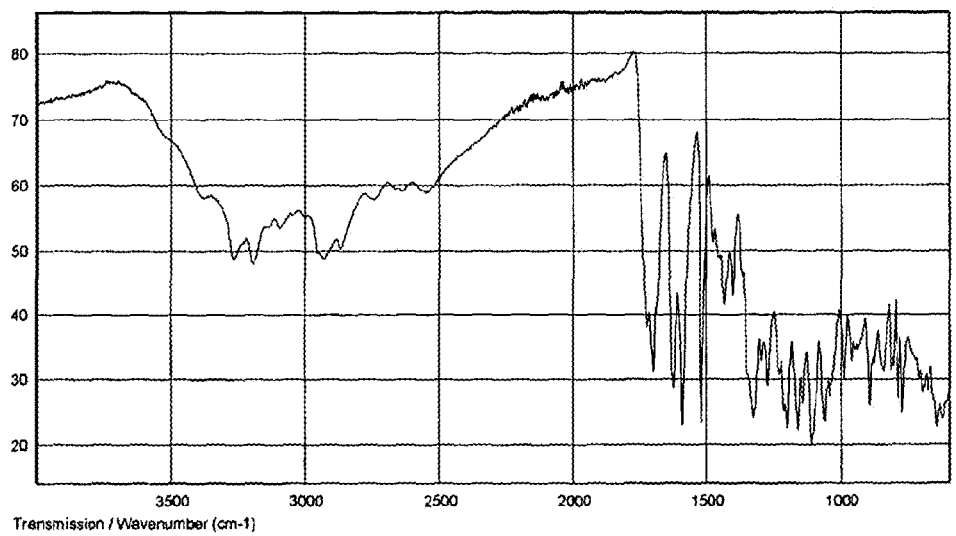
FIG. 18 shows infra-red spectrum of co-crystal of Compound A: succinic acid.

Infra-red spectroscopy data indicates presence of bands due to both Compound A and co-crystal former, but shifted (FIG. 18; little free succinic acid present in this sample). The shift in the positions of the peaks, particularly in the region of hydrogen bonding shows the form is not a simple physical mixture and is highly indicative of co-crystal formation. It should be noted that not all peaks are shifted, only those impacted by the change in interaction as a result of co-crystal formation. Peaks specific to the co-crystal Form A include 3263 (a), 3191 (a), 3091, 1722 (s), 1700 (s), 1591(a), 1520(a) $cm^{-1}$ and more specifically also include 1436, 1404, 1324, 1297, 1200, 1162, 1143, 1112, 1061, 1043 $cm^{-1}$ (where (s) and (a) peaks are unshifted with respect to s=succinic peaks and a=Compound A peaks).

Example 2-C

Compound A: Decanoic Acid Co-crystal Form A 50 mg of Compound A Polymorph II were ground for 2-3 minutes with a 1:1 molar equivalent of decanoic acid (16 mg), in the presence of approximately 15 microliters of acetonitrile. The solid went to a paste then became hard. The resulting solid was analysed by XRPD and Infra-red spectroscopy.

XRPD of the sample gave rise to diffraction pattern, with intense reflections due to the co-crystal at 14.27, 9.53, 8.65, 5.38, 4.31 Å and more specifically, 14.27, 10.81, 10.15, 9.53, 8.65, 8.26, 6.16, 5.95, 5.38, 5.07 and 4.31 Å.

FIG. 19 shows the XRPD pattern of Form A of the Compound A: decanoic acid co-crystal.

Figure 20:
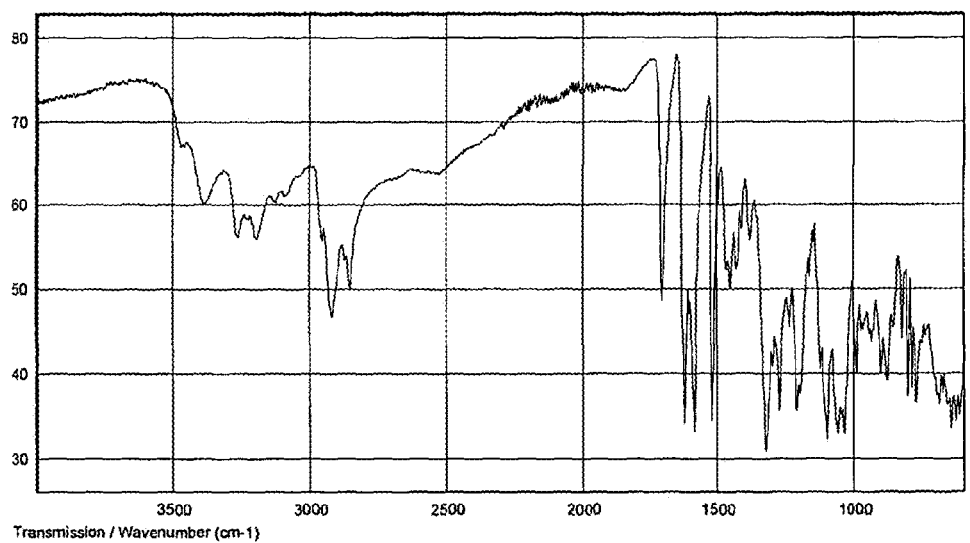
FIG. 20 shows infra-red spectrum of co-crystal of Compound A: decanoic acid.

Infra-red spectroscopy data indicates presence of bands due to both Compound A and co-crystal former, but shifted (FIG. 20). The shift in the positions of the peaks, particularly in the region of hydrogen bonding shows the form is not a simple physical mixture and is highly indicative of co-crystal formation. It should be noted that not all peaks are shifted, only those impacted by the change in interaction as a result of co-crystal formation. Peaks specific to the co-crystal Form A include 3465, 3381 (a), 3262 (a), 3190 (a), 2919, 2851, 2530, 1702 (d), 1588 (d), 1520 (d) cm$^{-1}$ and more preferably also include 1455, 1429, 1384, 1324, 1275, 1212, 1200, 1127, 1103, 1064 cm$^{-1}$ (where (d) and (a) peaks are unshifted with respect to d=decanoic acid peaks and a=Compound A peaks).

Example 2-D

Compound A: Salicylic Acid Co-crystal Form B

A saturated solution of salicylic acid was produced by saturating methanol with salicylic acid and filtering. Compound A was added to 1 mL of this saturated solution to form a light suspension. The suspension was stirred over 7 days at ambient temperature, adding more Compound A if dissolution had occurred. After 7 days, stirring was terminated. The resulting material was analysed by XRPD and Infra-red spectroscopy.

XRPD of the sample gave rise to intense reflections due to the co-crystal at 14.55, 11.00, 4.71 and 4.33 Å and more preferably, 21.09, 17.46, 14.55, 11.00, 6.31, 4.71 and 4.33 Å.

Figure 21:
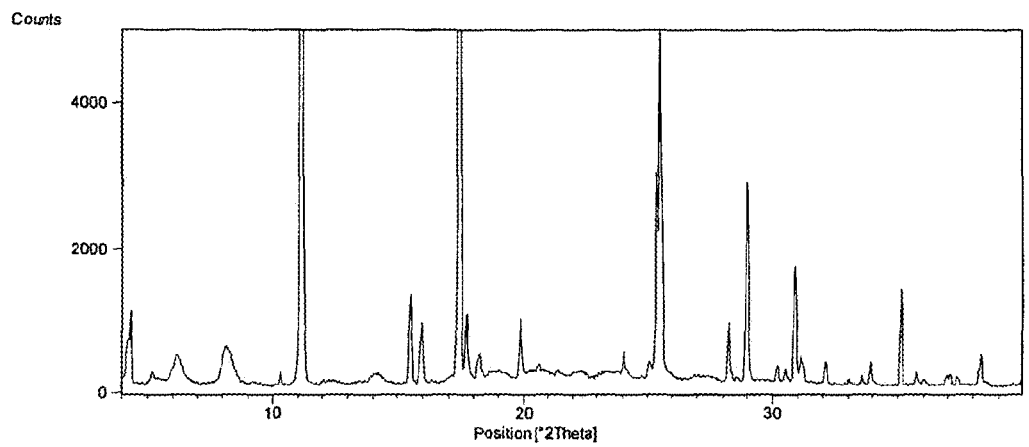
FIG. 21 shows an XRPD pattern of co-crystal of Compound A: salicylic acid Form B.

FIG. 21 shows the XRPD pattern of Form B of the Compound A: salicylic acid co-crystal. Note that the material contains co-crystal as well as salicylic acid as a physical impurity.

Figure 22:
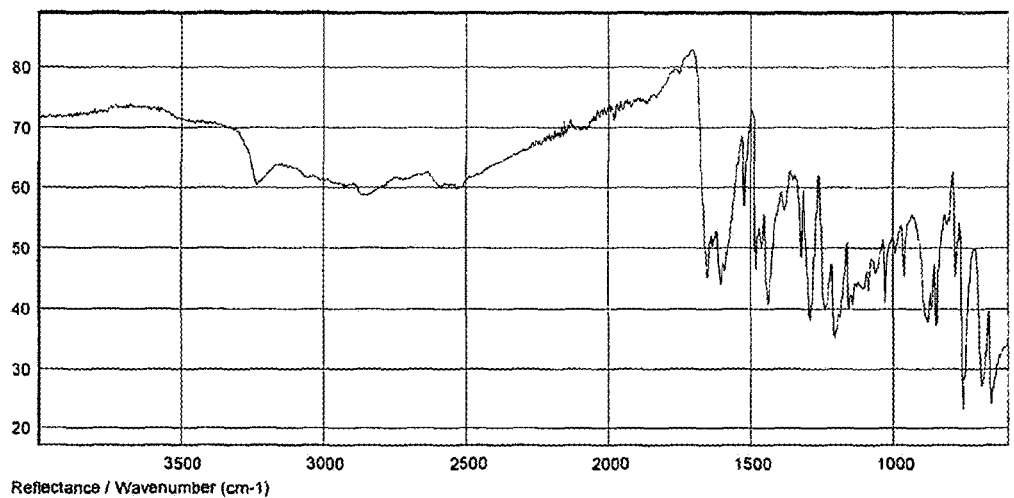
FIG. 22 shows infra-red spectrum of co-crystal of Compound A: salicylic acid Form B.

Infra-red spectroscopy data indicates presence of bands due to both Compound A and co-crystal former, but shifted (FIG. 22). The shift in the positions of the peaks, particularly in the region of hydrogen bonding shows the form is not a simple physical mixture and is highly indicative of co-crystal formation. It should be noted that not all peaks are shifted, only those impacted by the change in interaction as a result of co-crystal formation. Peaks specific to the co-crystal Form B include 1633 (s), 1590, 1522 (a) cm$^{-1}$ (where (s) and (a) peaks are unshifted with respect to s=salicylic acid peaks and a=Compound A peaks).

Example 2-E

Compound A: Gentisic Acid Co-crystal Form C

Figure 23:
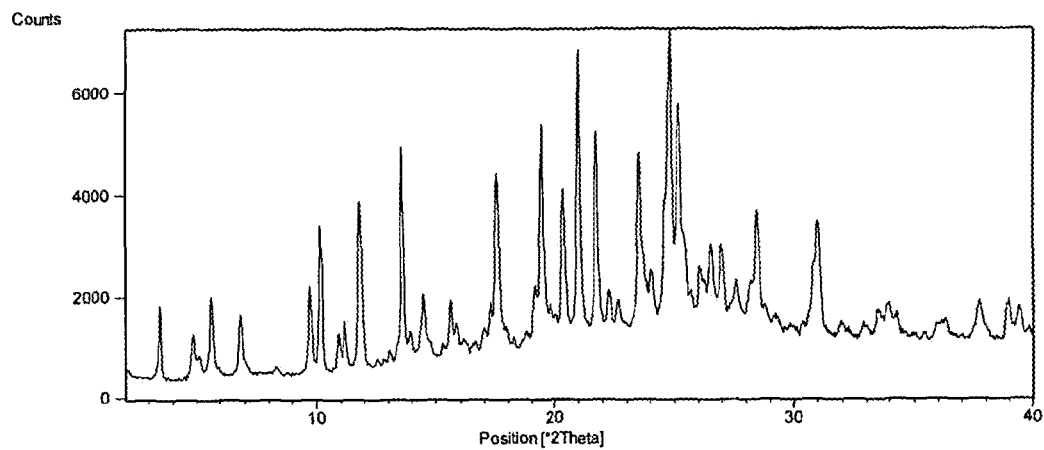
FIG. 23 shows an XRPD pattern of co-crystal of Compound A: gentisic acid Form C.

A saturated solution of gentisic acid was produced by saturating methanol with gentisic acid and filtering Compound A was added to 1 mL of this saturated solution to form a light suspension which later dissolved. The solution was left to evaporate (loosely fitted lid of vial). After 11 days, a solid had formed on which XRPD and Infra-red spectroscopy was performed XRPD of the sample gave rise to intense reflections due to the co-crystal at 25.52, 18.24, 15.77, 8.70, 7.49 and 4.23 Å and more preferably, 25.52, 18.24, 15.77, 12.96, 8.70, 7.49, 6.51, 5.06, 4.56, 4.36 and 4.23 Å. FIG. 23 shows the XRPD pattern of Form C of the Compound A: gentisic acid co-crystal.

Figure 24:
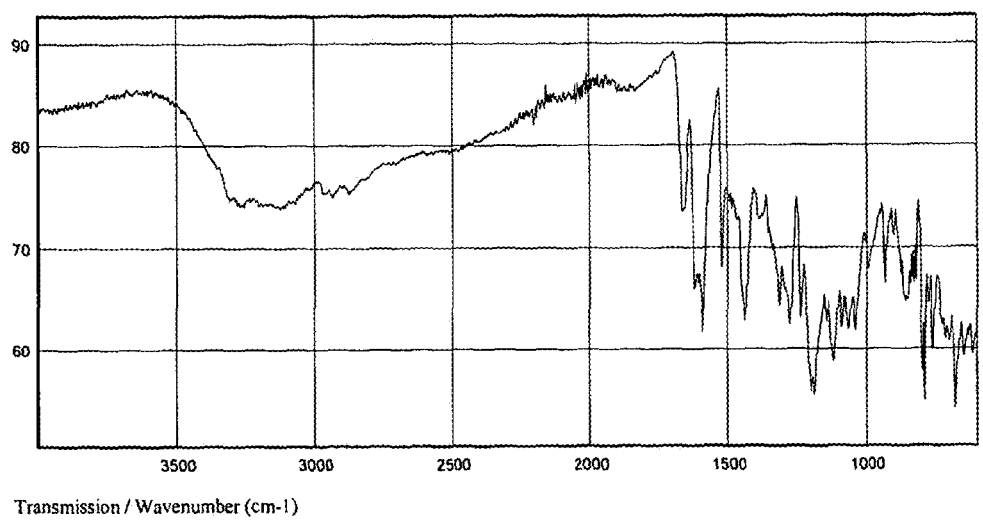
FIG. 24 shows infra-red spectrum of co-crystal of Compound A: gentisic acid Form C.

Infra-red spectroscopy data indicates presence of bands due to both Compound A and co-crystal former, but shifted (FIG. 24). The shift in the positions of the peaks, particularly in the region of hydrogen bonding shows the form is not a simple physical mixture and is highly indicative of co-crystal formation. It should be noted that not all peaks are shifted, only those impacted by the change in interaction as a result of co-crystal formation. Peaks specific to the co-crystal Form C include 3255 (g), 2969, 1521 (a) cm$^{-1}$ (where (g) and (a) peaks are unshifted with respect to g=gentisic acid peaks and a=Compound A peaks).

Example 3

Scale-up Work

API=Compound A (compound of formula (I))

Powder X-ray diffraction was recorded with a θ-θ PANalytical CUBIX (wavelength of X-rays 1.5418 Å Cu source, Voltage 45 kV, filament emission 40 mA). Samples were scanned from 2-40° 2θ using a 0.02° step width and a 100 second count time using an X'celerator detector (active length 2.55° 2θ).

Solution state NMR was performed as follows:

A sample of co-crystal (1-20 mg) was dissolved in ~0.75 ml of hexadeuterated dimethylsulphoxide (DMSO-d6) although in the case of the malonic acid samples, approximately 20 µl of trifluoroacetic acid (TFA) was also added to the sample. Samples were transferred to a 5 mm NMR tube. A proton (1H) NMR spectrum was recorded at 300K using a Bruker Avance 500 MHz spectrometer. The identity of API within the co-crystal samples was confirmed by comparison to a reference spectrum of API. For the stoichiometry measurements, accurate integrals were obtained for resonances from both the API (typically the aromatic resonance at 7.3 ppm) and the co-former, normalised for the number of protons and ratioed.

| Example 3-A: Compound A: malonic acid co-crystal Form A | |
|---|---|
| Mass API | 22.95 g |
| Mass co-former | 11.1 g |
| Mole fraction | 0.29 (API)/0.71 (co-former) |
| Solvent | acetone |
| Volume solvent | 50 mL |
| Relative volume | 1.67 mL/g (solids) |
| Initial temperature | 25° C. |
| Final temperature | 0° C. |
| Wash liquor | heptane |
| Volume wash liquor | 15 mL |
| Relative volume wl | 0.5 mL/g (solids) |

Solids were charged to a suitable, temperature controlled reactor equipped with a motorised agitator. The solvent was added and the temperature set to 25° C. After dissolution had occurred the temperature was reduced to 15° C. without any control over the cooling rate and the solution was left over night, during which time the co-crystals formed. After this time the slurry was cooled to 0° C. and left for 6½ hours. Thereafter the solids were filtered under vacuum, washed with heptane and dried at 40° C. under vacuum.

Characterisation of the sample by solution state nuclear magnetic resonance indicated that there was a 0.5 molar excess of malonic acid in the sample. A 2.0 g sample of malonic acid cocrystal was slurried in 4 mL acetone for 2 hour. To this suspension was then added a physical mixture of 1660 mg API and 348 mg malonic acid and left to stir over 2-3 days. The sample was then vacuum filtered and dried in a vacuum overnight at ambient temperature. The resultant dry sample was lightly ground. Solution state NMR indicated the overall API:co-former molar ratio was 1:1.1 showing a reduction to 0.1 molar excess of malonic acid.

XRPD was consistent with Form A of the malonic acid co-crystal.

Solid State NMR indicated the malonic acid co-crystal structure consists of only one crystallographically independent molecule of Compound A.

These data are indicative of a 1:1 stoichiometry of API:co-former in the co-crystal.

The malonic acid co-crystal so prepared was thermally stable up to 110° C.

| Example 3-B: Compound A: decanoic acid co-crystal Form A | |
|---|---|
| Mass API | 12.35 g |
| Mass co-former | 7.6 g |
| Mole fraction | 0.33 (API)/0.66 (co-former) |
| Solvent 1 | acetone |
| Volume solvent 1 | 40 mL (+10 mL) |
| Relative volume s1 | 2 mL/g (solids) (2.5 mL/g(solids)) |
| Solvent 2 | cyclohexane |
| Volume solvent 2 | 60 mL |
| Relative volume s2 | 3 mL/g (solids) |
| Initial temperature | 20° C. |
| Final temperature | 20° C. |
| Wash liquor | acetone/cyclohexane as a 1:1 (vol) mixutre |
| Volume wash liquor | 25 mL |
| Relative volume wl | 1.25 mL/g (solids) |

Solids were charged to a suitable, temperature controlled reactor equipped with a motorised agitator. The solvent was added and the temperature was set to 20° C. Due to a thermostat failure the temperature initially increased to 27° C. and dissolution of solids occurred. The temperature was reduced to 10° C. and crystallization occurred. The slurry was static at this temperature and the temperature was increased to 30° C. In contrast to the behaviour of the starting materials, the solids did not fully dissolve at this temperature, and the slurry becomes mobile. The temperature was then reduced to 20° C. The slurry was already static at 22° C. 3 relative volumes of cyclohexane (antisolvent) and ½ relative volume of acetone were added, resulting in a thick but stirrable slurry. The slurry was left at 20° C. over night. The slurry was then filtered, washed with a 1:1 mixture of acetone and cyclohexane and dried at 20° C. under vacuum.

Solution state NMR indicated the API:co-former molar ratio was 0.3.

XRPD was consistent with Form A of the decanoic acid co-crystal with excess Compound A Polymorph III (see WO 01/92262).

A person skilled in art will be able to manipulate the phase diagram to reduce any excess physical impurity and improve stoichiometry, as was performed in Example 3A. See, for example, Phase Solubility Diagrams of Cocrystals Are Explained by Solubility Product and Solution Complexation, Sarah J. Nehm, Barbara Rodríguez-Spong, and Naír Rodríguez-Hornedo Crystal Growth & Design, 2006, 6, 592-600.

| Example 3-C: Compound A: succinic acid co-crystal | |
|---|---|
| Mass API | 8.17 g |
| Mass co-former | 1.91 g |
| Mole fraction | 0.49 (API)/0.51 (co-former) |
| Solvent 1 | 2-propanol |
| Volume solvent 1 | 100 mL |
| Relative volume s1 | 9.9 mL/g (solids) |
| Solvent 2 | cyclohexane |
| Volume solvent 2 | 75 mL |
| Relative volume s2 | 7.4 mL/g (solids) |
| Initial temperature | 55° C. |
| Final temperature | 15° C. |
| Wash liquor | 2-propanol/cyclohexane as a 1:0.75 (vol) mixture |
| Volume wash liquor | 20 mL |
| Relative volume wl | 2 mL/g (solids) |

Solids were charged to a suitable, temperature controlled reactor equipped with a motorised agitator. The solvent was added and the temperature was set to 55° C.

The temperature was reduced to 15° C. and held for 10 hours. The slurry was then filtered, washed with a mixture of 2-propanol and cyclohexane and dried at 40° C. under vacuum.

Solution state NMR indicated the overall API:co-former molar ratio was 0.6

XRPD indicated the material was poorly crystalline.

A person skilled in art would be able to improve stoichiometry through manipulation of the phase diagram, as was performed for the malonic acid co-crystal.

| Example 3-D: Compound A: gentisic acid co-crystal Form D | |
|---|---|
| Mass API | 14.74 g |
| Mass co-former | 5.38 g |
| Mole fraction | 0.45 (API)/0.55 (co-former) |
| Solvent | acetone |
| Volume solvent | 50 mL |
| Relative volume | 2.5 mL/g (solids) |
| Initial temperature | 25° C. |
| Final temperature | 0° C. |
| Wash liquor | cyclohexane |
| Volume wash liquor | 20 mL |
| Relative volume wl | 1 mL/g (solids) |

Solids were charged to a suitable, temperature controlled reactor equipped with a motorised agitator. The solvent was added and the temperature was set to 25° C. The temperature was reduced to 10° C. over a period of 6 hours and the solution left at that temperature over night during which time crystallization occurred. The temperature was reduced to 0° C. and solids isolated once that temperature had been reached. The slurry was then filtered, washed with cyclohexane and dried at 40° C. under vacuum. XRPD and solution state NMR of this batch indicated poor crystallinity with an API:co-former molar ratio of 1:1.1 respectively.

The gentisic acid sample (2.2 mg) was first lightly ground then slurried in 5 mL of toluene over 2-3 days to improve crystallinity. The slurry became immobile during this time and was isolated and dried under vacuum at ambient temperature. The dried material was gently ground. XRPD was inconsistent with previous known forms, and was therefore denoted Compound A: gentisic acid co-crystal Form D (see FIG. 25). Solution NMR confirmed that the API:co-former molar ratio remained 1:1.1.

Figure 25:
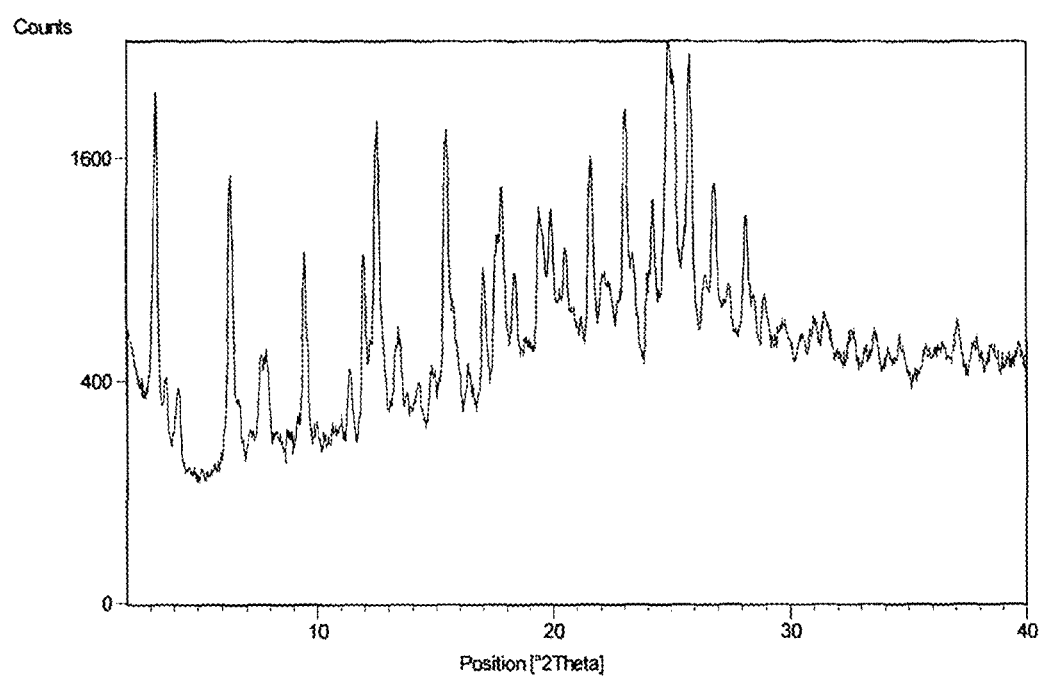
FIG. 25 shows an XRPD pattern of co-crystal of Compound A: gentisic acid Form D.

FIG. 25 shows the XRPD pattern of Form D of the Compound A: gentisic acid co-crystal.

TABLE 3-D-1

| Co-former | Form | Angle (° 2θ) | d-spacing (Å) |
|---|---|---|---|
| Gentisic acid | D | 3.24, 6.3, 9.5, 12.0, 12.5 | 27.2, 13.9, 9.4, 7.4, 7.1 |

TABLE 3-D-2

| Secondary peaks | | | |
|---|---|---|---|
| Co-former | Form | Angle (° 2θ) | d-spacing (Å) |
| Gentisic acid | D | 3.68, 4.20, 15.4 | 24.0, 21.0, 5.8 |

The gentisic acid co-crystal so prepared was thermally stable up to 137° C.

Example 4

Dissolution Work

Micro-dissolution investigations were performed by dissolving 9 mg of a sample of co-crystal in both 25 ml of (i) Fasted intestinal fluid (Fassif) without micelle forming components and (ii) of Simulated gastric Fluid (SGF).

The experiment demonstrated a 2-3 fold increase in solubility compared to Polymorph II of Compound A for Compound A: malonic acid co-crystal Form A and for Compound A: gentisic acid co-crystal Form D.

The invention claimed is:

1. A co-crystal of the compound {1S-[1α, 2α, 3β(1S*, 2R*),5β]}-3-(7-{[2-(3,4-difluorophenyl)cyclopropyl]amino}-5-(propylthio)-3H-1,2,3-triazolo [4,5-d]pyrimidin-3-yl)-5-(2-hydroxyethoxy)cyclopentane-1,2-diol of formula (I) and a co-former molecule

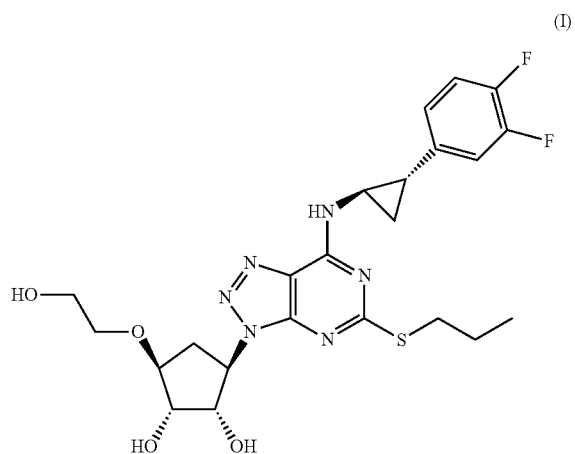 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

(I)

wherein the co-former molecule is selected from decanoic (capric) acid, succinic acid, or malonic acid.

2. A co-crystal of the compound of formula (I) according to claim 1, which is a crystalline form, selected from malonic acid co-crystal Form A, succinic acid co-crystal Form A, succinic acid co-crystal Form B, succinic acid co-crystal Form C, and decanoic co-crystal Form A.

3. A co-crystal of the compound of formula (I) according to claim 1, wherein each of said crystalline forms is characterised in that it has an X-ray powder diffraction pattern with peaks as shown in the following Table

| Co-former | Co-crystal Form | Angle (° 2θ) (measured at 1.5418 Å; except salicylic acid Form B measured at 1.5406 Å) |
|---|---|---|
| Malonic acid | A | 6.1, 9.6, 12.3, 14.4, 18.2 |
| Succinic acid | A | 3.9, 4.5, 6.5 |
| Succinic acid | B | 2.5, 3.5, 4.9, 6.9 |
| Succinic acid | C | 6.9, 7.7, 8.8, 14.1 |
| Decanoic acid | A | 6.2, 9.3, 10.2, 16.5, 20.6 | wherein 2-theta values are +/−0.2°.

4. A co-crystal of the compound of formula (I) according to claim 1, wherein each of said crystalline forms is characterised in that it has an X-ray powder diffraction pattern with peaks in addition to those in claim 3 as shown in the following Table

| Co-former | Co-crystal Form | Angle (° 2θ) (measured at 1.5418 Å; except salicylic acid Form B measured at 1.5406 Å) |
|---|---|---|
| Malonic acid | A | 21.1, 21.5, 25.8 |
| Succinic acid | A | 5.4, 8.4, 13.0, 25.5, 26.6 |
| Succinic acid | B | 10.1, 11.7, 13.8 |
| Succinic acid | C | 9.2, 11.5, 12.2, 12.7, 19.0, 21.1 |
| Decanoic acid | A | 8.2, 8.7, 10.7, 14.4, 14.9, 17.5 | wherein 2-theta values are +/−0.2°.

5. A co-crystal of the compound of formula (I) in crystalline form, according to claim 1, wherein the co-former molecule is malonic acid.

6. A co-crystal of the compound of formula (I) in crystalline form, according to claim 1, wherein the co-crystal is malonic acid co-crystal (Form A).

7. A method of preparing a co-crystal of the compound of formula (I) as defined in claim 1, said method comprising the step of mixing a solution of the compound of formula (I) free form with the appropriate co-former counter-molecule in a suitable solvent.

8. A pharmaceutical composition comprising a co-crystal of the compound of formula (I), as defined in claim 1, and a pharmaceutically acceptable diluent or carrier.

9. A method of treating arterial thrombotic complications in patients with coronary artery, cerebrovascular or peripheral vascular disease by administering a therapeutically effective amount of a co-crystal of the compound of formula (I) as defined in claim 1.

10. The method according to claim 7, wherein the suitable solvent is methanol.

11. A co-crystal of the compound of formula (I) in crystalline form, according to claim 1, wherein the co-former molecule is decanoic acid.

12. A co-crystal of the compound of formula (I) in crystalline form, according to claim 1, wherein the co-former molecule is succinic acid.

13. A co-crystal of the compound of formula (I) in crystalline form, according to claim 1, wherein the co-crystal is succinic acid co-crystal (Form A).

14. A co-crystal of the compound of formula (I) in crystalline form, according to claim 1, wherein the co-crystal is succinic acid co-crystal (Form B).

15. A co-crystal of the compound of formula (I) in crystalline form, according to claim 1, wherein the co-crystal is succinic acid co-crystal (Form C).

16. A co-crystal of the compound of formula (I) in crystalline form, according to claim 1, wherein the co-crystal is decanoic acid co-crystal (Form A).

* * * * *